United States Patent
Binning et al.

(10) Patent No.: US 7,452,466 B2
(45) Date of Patent: *Nov. 18, 2008

(54) METHOD AND APPARATUS FOR ANAEROBIC DIGESTION OF BIOMASSES AND GENERATION OF BIOGAS

(76) Inventors: Rupert Binning, Moselstr 27, D-54341 Fell (DE); Fritz Mödinger, Sciaves 104, I-39040 Naz Sciaves (Bz) (IL); Paul Gasser, Sciaves 104, I-99040 Naz Sciaves (Bz) (IL)

(*) Notice: Subject to any disclaimer, the term of this patent is extended or adjusted under 35 U.S.C. 154(b) by 153 days.

This patent is subject to a terminal disclaimer.

(21) Appl. No.: 11/261,997

(22) Filed: Oct. 28, 2005

(65) Prior Publication Data

US 2006/0060526 A1    Mar. 23, 2006

Related U.S. Application Data

(63) Continuation-in-part of application No. 10/836,474, filed on Apr. 30, 2004.

(30) Foreign Application Priority Data

Apr. 30, 2003    (IL) .......................... BZ2003A0024

(51) Int. Cl.
   *C02F 3/28*    (2006.01)
   *C02F 11/04*    (2006.01)

(52) U.S. Cl. ........................ 210/603; 210/614; 210/259

(58) Field of Classification Search ................. 210/603, 210/612, 614, 252, 259; 71/10; 435/262.5
See application file for complete search history.

(56) References Cited

U.S. PATENT DOCUMENTS

| | | | | |
|---|---|---|---|---|
| 4,318,993 | A * | 3/1982 | Ghosh et al. | 435/294.1 |
| 4,442,006 | A * | 4/1984 | Ishida et al. | 210/613 |
| 4,597,872 | A * | 7/1986 | Andersson et al. | 210/605 |
| 4,652,374 | A * | 3/1987 | Cohen | 210/603 |
| 5,525,229 | A * | 6/1996 | Shih | 210/603 |
| 5,529,692 | A * | 6/1996 | Kubler | 210/603 |
| 5,630,942 | A * | 5/1997 | Steiner | 210/603 |
| 6,663,777 | B2 * | 12/2003 | Schimel | 210/603 |

FOREIGN PATENT DOCUMENTS

DE    19623163    * 12/1996

* cited by examiner

*Primary Examiner*—Fred Prince
(74) *Attorney, Agent, or Firm*—Horsi M. Kasper

(57) ABSTRACT

A method and apparatus for an anaerobic digestion of biomasses with generation of biogas and sludge, wherein a hydrolyzation phase and a following fermentation of the biomass are included, wherein a hydrolyzation phase (5) and at least two following fermentation phases (7,8,9) are included and wherein the hydrolyzation (5) as well as the following fermentations (7,8,9) are performed in separate containers with specific measurement and control of the temperature, of the mixing degree, of the pH value and of the pressure.

20 Claims, 2 Drawing Sheets

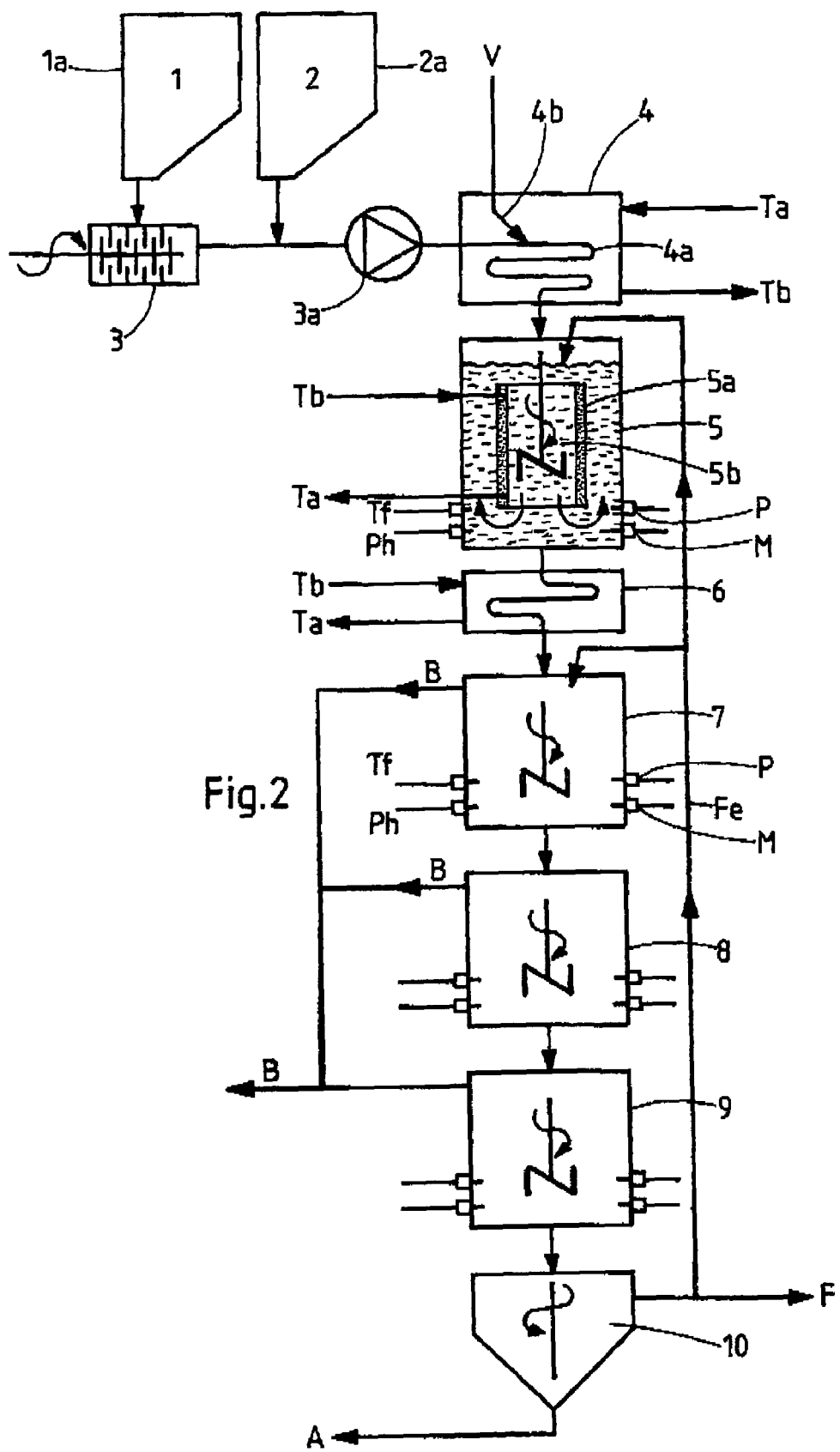

US 7,452,466 B2

METHOD AND APPARATUS FOR ANAEROBIC DIGESTION OF BIOMASSES AND GENERATION OF BIOGAS

RELATED APPLICATIONS

This application is a Continuation-in-part application of another application bearing Ser. No. 10/836,474 and filed on Apr. 30, 2004 and to be abandoned

BACKGROUND OF THE INVENTION

1. Field of the Invention

The invention relates to a method and to an apparatus for anaerobic digestion of biomasses of different origin, consistency and chemical properties for the production of biogas.

2. Brief Description of the Background of the Invention Including Prior Art

Methods for the production of biogas with a fermenting machine or reactor are known, wherein complex organic materials (lipids, protids, glucids), which materials are contained in plants or in animal residual products, are destroyed and thereby enable to obtain energy by way of chemical reaction with the aid of enzymes, fungi and microorganisms, wherein these are formed in the biomass in the substrate of a biological origin (organic mass) under in each case defined process conditions. The fermentation is performed thanks to a non-aerobic flora of bacteria, which flora of bacteria is formed depending on the temperature prevailing in the fermentation machine. These bacteria are contained in the biomass and strongly multiply in a closed environment, wherein the enzymes serve as a catalyst; the enzymes react with the organic materials mostly to $CH_4$ (methane) and $CO_2$ (carbon dioxide).

The known methods and the plants for their realization do not take sufficiently into consideration that the non-aerobic flora of bacteria is formed of strains of bacteria, which strains of bacteria develop optimally at in each case specific temperatures between 25 degrees centigrade and 45 degrees centigrade and under specific environmental conditions. In addition there exists the risk that a too pronounced acidification occurs during the acidification phase caused by the formation of free acids and therefore the control of the pH value becomes difficult. This causes that the times, within which the individual process steps run, are becoming increased or, respectively, that the residues of the fermentation process are obtained which are not suitable for an advantageous employment of the process, since the residues contain not reacted or only partially reacted components. A too strong acidification can also cause the interruption of the biological course and therewith of the fermentation process. The precedingly recited methods and the corresponding apparatuses do not sufficiently take into consideration the influence of the temperature on the reaction and more generally those of the environmental situations under which the degradation reactions occur. In particular, the conditions for too high an acidification can occur during the phase of the acid formation. The too high formation of free acids and therewith difficult control of the pH values effects a slowing down of the course of the reaction and an incomplete conversion of the substrate with successive maintaining of residual products which are not suitable for later use because of the high content in organic materials.

SUMMARY OF THE INVENTION

1. Purposes of the Invention

It is an object of the present invention to realize a suitable method for the anaerobic digestion of biomasses of the above recited kind as well as a suitable apparatus for this purpose, by way of which the conversion of the biomass is enabled, often the substrate of a biological origin (organic mass) for the purpose of processing biological waste of different origin, different particle size and consistency with different carbon to nitrogen C/N ratios and different humidity, with simultaneous optimation of the duration of the fermentation or, respectively, digestion process, with simultaneous increase of the degree of conversion of the methanogenous substrate, in order to obtain in this manner solid and liquid residues, which solid and liquid residues can be employed as a component in other production processes or in the same production process (recycling) or in different production cycles or in a recycling process.

It is a further object of the present invention to obtain the following advantages:
obtaining a higher yield of biogas,
obtaining solid and liquid residual volumes, which are suitable for the use as additives in production processes.

It is another object of the present invention to furnish a recovery process, where the reactions are performed under favorable conditions.

It is a further object of the invention to improve control of anaerobic digestion of biomasses.

These and other objects and advantages of the present invention will become evident from the description which follows.

2. Brief Description of the Invention

The present invention furnishes a method for achieving an improved anaerobic digestion of biomasses, wherein the method is subdivided as follows:

a specific pre-treatment of the diverse biomasses or of parts of the biomasses involving a mechanical comminution and/or a steam treatment and/or the heating to temperatures which effect a "hygienization" of the biomasses;

a cascade fermentation in order to create ideal conditions for the in each case specific requirements of the individual strands of the flora of the period in order to obtain in particular a methanization during several stages and separate from the acidification phase;

the feeding back of a part of the sludge, which sludge is produced in the last stage of the process, into the phases of hydrolysis and/or of fermentation with the purpose of feeding in of enzymes, which enzymes operate as biological catalysts;

the thickening of the sludge by way of a hydro cyclone through separation of residual liquids.

For resolving the object of the present invention there is disclosed a method, which is subdivided in the following way:

hydrolysis of the poly saccharides, of the proteins, of the lipids;

acidification under formation of simple biological acids;

single or multi-step methanization;

in order to obtain thereby an easier control of the pH value by separating the acidification step from the methanogenous step and by creating the in each case ideal conditions for the specific requirements of the individual bacteria strains of the anaerobic flora of bacteria by furnishing of a cascade fermentation.

The course of anaerobic digestion is performed essentially in three phases:

hydrolysis of the cellulose, of the sugars and of the amino acids;

acidic phase for forming of simple organic acids (for example acetic acid) and alcohols (for example ethyl alcohol);

methane formation by way of methanogenic bacteria through reaction of acids and alcohols into methane and carbon dioxide.

Hydrolysis, acidification, and methane generation

Hydrolysis, acidification, and methane generation have been described as biochemical processes, which have been realized on a large-scale. The present application does not teach many of the basic technical features of the individual underlying processes but is directed toward the spacial separation and the sequential performance of the processes in a cascade procedure.

Hydrolysis means that sugar, fats, and proteins are disintegrated into their basic building blocks. An important feature of the present method is the spacial separation of the hydrolysis based on the different compositions of the materials to be fermented. This is associated with the advantage that the bacteria, which are responsible for the hydrolysis of different starting materials, encounter in each case the best preconditions. Bacteria involved in sugar hydrolysis prefer a temperature of about 60 degrees centigrade. Bacteria involved in hydrolysis of proteins prefer a temperature of about 60 degrees centigrade. Bacteria associated with the hydrolysis of starches preferred temperatures around 90 degrees centigrade. Bacteria associated with the fat hydrolysis thrive best at an ambient temperature of 40 degrees centigrade. The coordinated separation of the processes depending on the starting material is a basic new feature of the present method.

The apparatus of the invention comprises:
a cutting plant for the comminution of the biomasses, which cutting plant is employed in particular for the biomasses with a carbon to nitrogen C/N ratio higher than 30 and a humidity content under 30 percent;
a fermentation machine which comprises separate and different reactors for the purpose of a more effective control of the reaction conditions of the individual process phases;
a heat treatment with the introduction of hot water vapor directly into the stream of the biomass and/or with a heat exchanger in order to obtain the "hygienization" of certain biomasses (for example starch containing biomasses);
a heat exchanger for bringing the temperature of the biomass at the discharge after the hydrolysation process to the ideal value for the following acidification process;
the obtained thermal energy can be used for pre-heating or for feeding thermal energy in one or in several process phases.

The different devices of the apparatus plant are equipped with thermal sensors and mixers in order to obtain the optimal thermal conditions for the in each case optimal effect of the specific strains of bacteria.

The novel features which are considered as characteristic for the invention are set forth in the appended claims.

The invention is illustrated by way of the accompanying drawings. The accompanying drawings represent schematically the course of the process according to the present invention or, respectively, the apparatus plant according to the present invention for an anaerobic digestion of biomasses of different origin, consistency, and chemical properties, for the generation of biogas, thickened sludge, and liquid residual materials. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention:
FIG. 2 shows a block diagram of the apparatus and according to the present invention, wherein the apparatus plant operates according to the method presented in FIG. 1.

DESCRIPTION OF INVENTION AND PREFERRED EMBODIMENT

Figure 1:
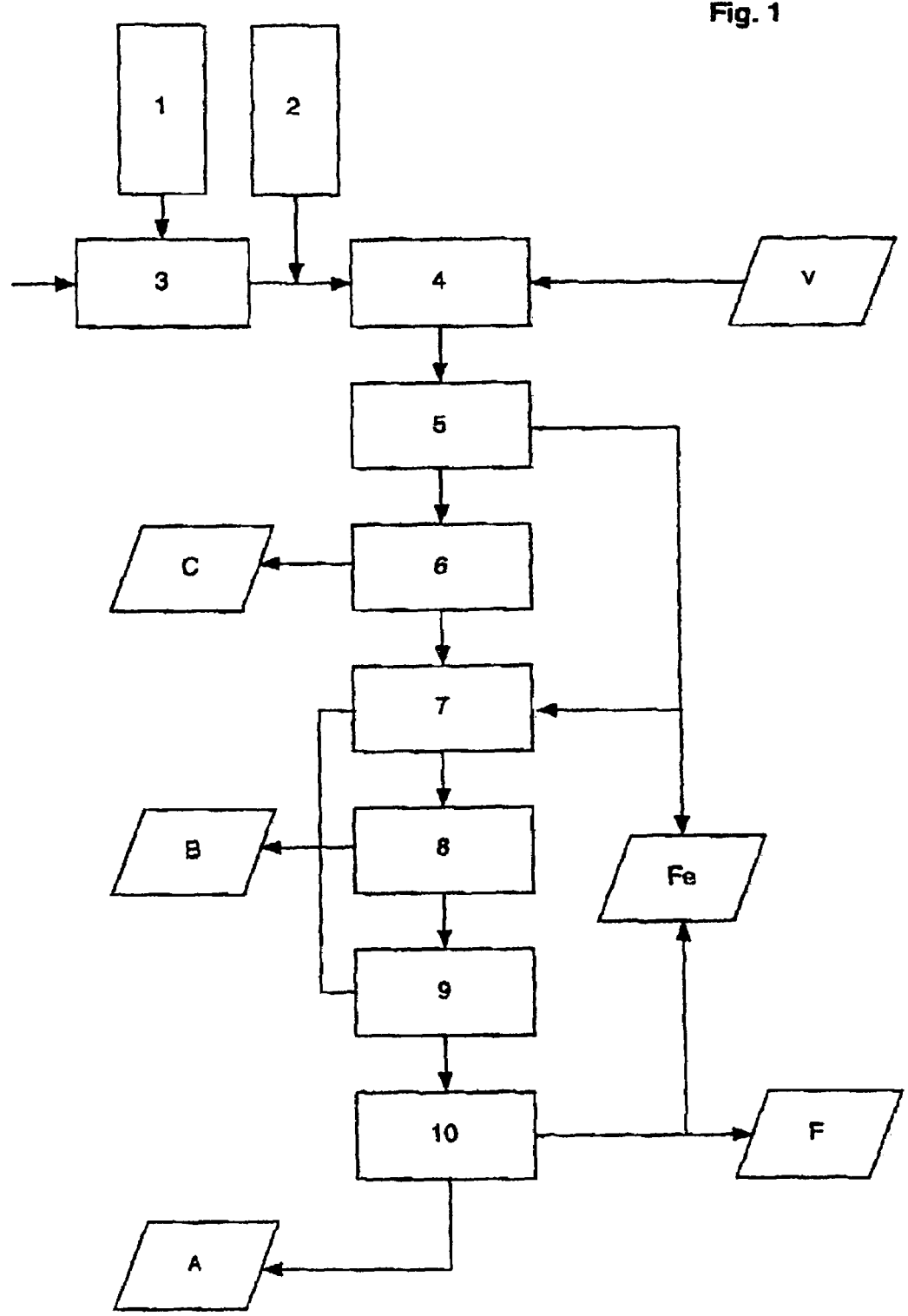
FIG. 1 is a view of a block diagram of the invention method.

The method of the Invention involves defining the major reactions of anaerobic digestion of biomass, substantially separating these steps by inducing a sequence of reaction steps, wherein the reaction steps furnish optimum conditions for sequentially performing the respective major reactions.

The method of the present invention generally comprises the following steps under defined conditions:
Comminuting a biomass,
Hydrolyzing the comminuted biomass,
Acidifying the hydrolyzed biomass
Generating methane in the acidified biomass.

A biomass is defined by originating from plants and animals. Examples of biomasses are carbon deposits, coals, oil deposits, oil shale, gas deposits, trees, composted leaves, waste discharges, food processing residues, paper residues, animal waste, fruits, grains, fish flour.

Comminuting is defined as reducing the grain size of the biomass.

The starting grain size of the processed biomass can be from about anything to 10 centimeters.

The grain size of the processed biomass after comminuting can be from about 0.1 to 10 millimeters and is preferably smaller than 1 millimeter.

Hydrolyzation is defined as splitting up of ether bonds or of ester bonds of organic materials of the biomass..

The comminuted biomass will contain a number of ether bonds per kilogram and hydrolyzation means that at least 70 percent by weight and preferably 90 percent by weight of the ether bonds become hydrolyzed.

The comminuted biomass will contain a number of ester bonds per kilogram and hydrolization means that at least 70 percent by weight and preferably 90 percent by weight of the ester bonds become hydrolyzed.

The hydrolyzed biomass will have a pH value in the range from pH 4 to pH 10.

The acidified biomass will have a pH value in the range of from pH 2 to pH 5.

The methane generation is defined as an anaerobic reaction of at least 50 molar percent of acetyl groups present in the acidified biomass to methane.

The method of the present invention will now be set forth in detail.

The biomass digestion process of the present invention is based upon the spatial separation of certain biological processes into separate phases.

A biomass mixture of 1,2 is taken from storage facilities or silos 1a, 2a, which contain bio waste 1 of the type of a large or coarse particle size with a carbon to nitrogen C/N ratio larger than about 30 and a humidity content under 30 percent and organic sludges 2 and/or biomasses of fine particle size with a molecular carbon to nitrogen C/N ratio advantageously below 30 and a content in humidity of advantageously above 30 percent. A coarse particle size has particle diameters up to 5 cm. A fine particle size has particle diameters from 0.1 mm to 1 mm and preferably not larger than 0.5 millimeters.

Conditions of cutting and comminuting

Cutting and comminuting refers to a purely mechanical process. The concepts aerobic and, respectively, anaerobic refer to reaction conditions which are performed in the presence of oxygen or, respectively, in the absence of oxygen. The chemical concepts of aerobic and anaerobic do not play a part in this context, since the cutting and comminution are independent of the chemical reaction conditions.

The charging volume of the starting biomass is fed to the cutting plant 3 for the purpose of comminuting into smaller particle sizes and is then fed to a pre-heater by way of a pump 3a, where the biomass is subjected to a heat addition (Ta-Tb) with the heat exchanger 4a. If required, water vapor V can be employed for this purpose, wherein the water vapor can be injected in the charging region, in the discharging region of the heat exchanger, into the biomass or into the heat exchanger itself.

The water content of the comminuted biomass can be from about 40 to 80 weight percent and is preferably from 50 to 70 weight percent. The temperature of the comminuted biomass prior to hydrolysis can be from about ambient temperature to 100 degrees centigrade. The temperature of the comminuted biomass preferably is within 10 degrees of the temperature maintained in the following hydrolyzation tank. The above recited thermal treatments can be required for the hygienization of the biomass and/or for the thermal splitting of the starches. Usually the pre-heating in the biomass effects a temperature which doesn't surpass 100 degrees centigrade. Thereupon the biomass is fed to the hydrolyzer, which hydrolyzer as well as the following fermentation machines 7,8,9, are equipped with a vertically standing double walled tube 5a, wherein a cooling agent (Tb-Ta) or, respectively, a thermal medium circulates inside the double walled tube 5a for controlling the temperature. In a first stage of the biomass digestion process the biomass is hydrolyzed, a chemical process in which a molecule is cleaved into two parts by the addition of a molecule of water and/or treated with enzymes as a catalyst. The used enzymes can be but are not limited to proteins and their complexes such as Oxidoreductases Transferases and/or Transferases and/or Hydrolases Transferases and/or Lyases Transferases and/or Isomerases Transferases and/or Ligases or any combination of the aforementioned. The hydrolysis enzymes are added to the comminuted biomass in an amount of from about 0.1. gram to 1 gram per kilogram of biomass. A separate addition of hydrolysis enzymes can be avoided in cases where it is possible to feed back reacted biomass containing hydrolysis enzymes.

In order to have sufficient amounts of corresponding bacteria present, the reaction containers can be associated with the respective fermentations storage, wherein the fermentation storage is connected to the input of the container and to the output of the container. The fermentation storage is fed from the output of the container containing substantial amounts of enzymes and bacteria, wherein the enzymes and bacteria are then re-entered into the container at the input side. This feature can be separately provided for the hydrolysis reactor, the acidification reactor, and/or the methane generating reactor.

The input of the hydrolysis reactor can contain materials which advance the hydrolysis in the hydrolysis reactor. These can be enzymes and bacteria which advance the hydrolysis reaction. This can be steam for adjusting the temperature during hydrolysis. This can be water for reducing the overall viscosity of the material subject to hydrolysis.

The anaerobic hydrolysis

All biochemical processes including the methane generation are anaerobic: during the hydrolysis, the biopolymers which are chemical compounds comprising chain or branch molecules, are disintegrated in their basic building blocks and other water-soluble decomposition products. It can be noted here that the fats are decomposed into fatty acids, that the carbohydrates such as for example poly saccharides are decomposed into mono or oligo saccharides and that the proteins such as albumin are decomposed into peptides or, respectively, amino acids. This reaction can be catalyzed as desired by anaerobic microorganisms. As desired means here is that the biochemical reaction does not have to be performed in a complete absence of oxygen. Residual traces of oxygen do not necessarily impede the reaction. The hydrolysis bacteria perform the hydrolysis based on discharge of enzymes. This reaction step is the speed determining step based on the complexity of the starting materials.

The preferred reaction temperature for hydrolysis is to be found between 35° C. and 90° C. but can be, for specific biomasses, decreased or increased. The reaction time is usually to be found between 1 and 24 hours depending on the type of biomass.

Bacteria involved in sugar hydrolysis prefer a temperature of from about 50 to 70 degrees centigrade. Bacteria involved in hydrolysis of proteins prefer a temperature of from about 50 to 70 degrees centigrade. Bacteria associated with the hydrolysis of starches preferred temperatures from about 80 to 100 degrees centigrade. Bacteria associated with the fat hydrolysis thrive best at an ambient temperature of from about 30 to 50 degrees centigrade. The temperature of the hydrolysis container is set depending on the contents of the biomass in proteins, sugars, starches or fats. If different components (proteins, sugars, starches or fats) are simultaneously present in the biomass, then it can be advantageous to use two or three separate hydrolysis containers to be connected sequentially for providing an optimized and substantially complete hydrolyzation of the biomass. For example, a first hydrolysis container connected to the cutting apparatus operates at temperatures from about 30 to 50 degrees centigrade for hydrolyzing the fats, a second hydrolysis container sequentially connected to the first hydrolysis container operates at temperatures of from 50 to 70 degrees for hydrolyzing the sugars, and a third hydrolysis container connected to the acidifying container and sequentially connected to the second hydrolysis container operates at a temperature of from about 80 to 100 degrees centigrade for hydrolyzing the starches. Alternatively, the first hydrolysis container connected to the cutting apparatus operates at temperatures from about 80 to 100 degrees centigrade for hydrolyzing the starches, the second hydrolysis container sequentially connected to the first hydrolysis container operates at temperatures of from 50 to 70 degrees for hydrolyzing the sugars, and the third hydrolysis container connected to the acidifying container and sequentially connected to the second hydrolysis container operates at a temperature of from about 30 to 50 degrees centigrade for hydrolyzing the fats.

According to a preferred embodiment the hydrolysis reaction container can be provided as two or three sequential containers, wherein one container serves for the thriving of the fat hydrolysis bacteria at a temperature of about 40 degrees centigrade, wherein a second container serves for the thriving of the sugar hydrolysis bacteria and/or the protein hydrolysis bacteria at a temperature of about 60 degrees centigrade, and wherein a third container serves for the thriving of the starch hydrolysis bacteria at a temperature of about 90 degrees centigrade. Preferably the first container is for fat hydrolysis, the second container for sugar hydrolysis and protein hydrolysis, and the third container for starch hydrolysis.

The biomass needs to be mixed continuously during hydrolysis either by a compulsory mixing system with mixing paddles for example. In case of employing an internal mixer such as tube mixer with upwards or downwards flow direction, then a downwards flow is to be preferred in order to avoid the formation of sedimentary deposits at the bottom of the vessel. Mixing can be either continuously or intermittent whereas it has been shown that stopping mixing during the loading phase of the first vessel is advantageous.

The hydolysis is performed by operation of the respective enzymes in the hydrolysis reactor 5 preferably under specific surveillance and monitoring of the temperature with a temperature sensor (Tf), of the pressure with a pressure sensor (P), of the pH value with a pH-sensor (Ph), of the intermixing with an intermixing sensor (M) and of the gas discharge.

The hydrolysis according to the present invention takes place at temperatures between 40 degrees centigrade and 100 degrees centigrade in order to split the organic polymer substrates such as complex starches, pectin, hemicelluloses in the presence of and under interaction with hydrolysis enzymes (amylases, pectinases, hemicellulases), whereby predominantly mono saccharides and a substrate of low viscosity are formed, which substrate is thereby better available and better suited for the successive activity of the methanogenus bacteria.

The following steps are taken to control the reaction and to avoid that the hydrolysis is accompanied by acidification and/or methane formation.

Heat transferred to the biomass to be hydrolyzed with the aforementioned heat exchanger systems must be regulated in order to maintain the process temperature in the specific vessel at the desired temperature +/−5° C. Such regulation might be achieved by increasing or decreasing the flow of the heat exchanger medium by means of automatically controlled valves or by increasing or decreasing the temperature of the heat exchanger medium itself.

The hydrolysis stage is conventionally furnished for the generation of biogas. However a favorable generation of biogas occurs at substantially lower temperatures as compared with conventional hydrolysis temperatures. Conventionally, a hydrolysis reaction with biogas production occurs without a control of the temperature and of the intermixing depending on the properties and the concentration of biomass.

The hydrolysis is performed under anaerobic conditions.

In contrast, according to the present invention enzymes (amylases, pectinases, hemicellulases) or other materials such as for example several ferments can be added during the hydrolysis of the biomass, whereby eventually also a partially controlled feedback Fe of the sludges F is furnished, wherein the sludges F are taken out at the end of the course of the process.

Preferably, the following materials are added to the biomass during the hydrolysis stage: steam for controlling temperature and viscosity, hydrolysis enzymes and biomass feedback.

It is suitable to cool the hydrolyzed biomass substrate in a heat exchanger prior to feeding the hydrolyzed biomass substrate into the fermenting machines 7,8,9, wherein possibly the heat is transferred to the cooling medium Tb-Ta, wherein then the cooling medium can be employed for the warming or pre-warming of the devices or of parts of the same plant or of a plant connected thereto.

The fermentation (acidification and methane generation) is performed like a cascade in separate fermenting machines 7,8,9 according to the present invention, wherein the separate fermenting machines 7,8,9 are in each case individually controllable and wherein specific cultures that directedly operate under optimum conditions relative to temperature, to intermixing, to the discharge of gas and to the pH value.

The optimum conditions are defined as follows:

It is known that the different anaerobic strains of bacteria develop their optimum activity of acidification in each case at different temperatures: the psicrophilous bacteria at temperatures below 15 degrees centigrade, the mesophilous bacteria at temperatures between 25 degrees centigrade and 45 degrees centigrade, and the thermophilous at temperatures above 45 degrees centigrade.

The formation of acids and/or the acidification by operation of the acid bacteria is performed in the first fermenting machine 7 always under specific surveillance and monitoring of the temperature with a temperature sensor (Tf), of the pressure with a pressure sensor (P), of the pH value with a pH-sensor (Ph), of the intermixing with an intermixing sensor (M) and of the gas discharge. The main culture strains are of the type *lactobacillus* (for example *lactobacillus casei, lactobacillus plantarum*) and of the type *streptococcus* (for example *streptococcus lactii, streptococcus cemoris*).

The input of the acidification reactor can contain materials which advance the acidification in the acidification reactor. These can be acidification bacteria and enzymes as well as pH controlling materials.

The anaerobic acidification

Like the hydrolysis, the acidification is as desired an anaerobic process. In the context of the acidification oxidation processes are running, however oxidation does not mean that free oxygen radicals have to be president. Oxygen containing compounds such as sulfate or nitrates are employed as electron acceptors instead of oxygen.

The fermentation for acidification

The acidification is performed in a common tank and at a pH value of from about 3 to 4. The electrical conductivity is small. After performing the acidification, the liquid containing acetic acid is led into the container where the methane generation is to take place.

The hydrolyzed biomass is then transferred into the acidification vessel by means of suitable pump such as a positive displacement pump or a centrifugal pump, with a constant or intermittent flow. It has been shown to be of advantage to interrupt mixing during acidification. It is preferred to transfer the hydrolyzed biomass from the bottom of the hydrolyzation vessel to the top of the acidification vessel. Acidification takes place at pH values in the range of 3 to 5 and at temperatures in the range of 25° C. to 65° C. Piping has to be dimensioned accordingly to the capacity of the pump, wherein flow speeds of 4 to 5 cm/sec are best suited for the purpose.

Following hydrolyzation and acidification, the preparatory process of the biomass, the acidified biomass is fed to the methane generators either by overflow from the acidification vessel or by a pump of the aforesaid type. In case of overflow this occurs whenever biomass is fed to the acidification vessel from the hydrolyzation vessel and hence the level in the acidification vessel reaches the point of overflow.

The proper methanogenus bacteria operate in the following fermenting machines 8,9, wherein the methanogenus bacteria require the controlled feeding of bio genous acids in the acidified biomass substrate coming from the fermenting machine 7. Mixed cultures, predominantly of the type the methanobacterium, methanosarcina, and methanococcus, operate in these fermenting machines. Cellulitis bacteria operate in symbiosis with the methanogenus bacteria, wherein the cellulitis bacteria effect the hydrolysis and the digestion of the organic materials with low solubility, such as for example cellulose.

Methane is produced by bacteria. The bacteria are anaerobes and operate only in anaerobic environments (no free oxygen). Constant temperature, pH and fresh organic matter promote maximum methane production.

The input of the methane generating reactor can contain materials which advance the methane generation in the methane generator. Such materials can be methane generating bacteria, acids or bases for controlling an appropriate pH value.

The anaerobic generation of methane

The methane generation is necessarily an anaerobic process, which means that no free oxygen radicals can be present in this process, since the catalytically acting bacteria do not have any protective mechanism against the oxygen radicals. This however does not exclude that the oxidation processes occur in connection with the methane generation. Oxygen containing compounds such as sulfate or nitrates are employed as electron acceptors instead of oxygen. Acetic acid generated during the acidification is transformed in the synthesis of methane by corresponding acetoclastic and acetic acid cracking formers of methane into methane and carbon dioxide as well as hydrogen.

Generation of methane

The generation of methane is preferably performed at the pH value of from about 7 to 8 and at a temperature of about 37 degrees centigrade.

Temperatures usually are maintained at from about 30 to 60 degrees centigrade and at approximately 40° C. during methane formation. Other temperatures can be used if held constant. For each 5° C. temperature decrease, gas production will be cut approximately one half or will take twice as long. A constant temperature is critical. Temperature variations of as little as 0,5° C. can inhibit the methane-formers enough to cause acid accumulation and possible digester failure.

The formation of methane by operation of the methanogenous bacteria is performed in the first and second biogas forming vessels 8, 9 preferably under specific surveillance and monitoring of the temperature with a temperature sensor (Tf), of the pressure with a pressure sensor (P), of the pH value with a pH-sensor (Ph), of the intermixing with an intermixing sensor (M) and of the gas discharge.

The methane-formers break down the acids into methane and carbon dioxide. Since these anaerobic and methane forming bacteria multiply only very slowly, and since an anaerobic metabolism exhibits a small energy density, it is necessary to furnish a partial feedback Fe of the sludge F generated at the end of the process into the first phases of the fermentation 5,7.

The methanogenus bacteria are present in nearly all materials, which are subject to an anaerobic disintegration (sewage sludge, moor sludge, swamp sludge, mining sludge) and are also present in the stomach of the ruminants in symbiosis, and for this reason the excrements of the ruminants are suitable as easily available starting cultures.

The separation of the reaction procedures

Important parameters are captured in the cutting plant 3, namely the temperature, the electrical conductivity and the pH value. The temperature is a very important parameter and in contrast to simple chemical reactions the reaction speed is more complex in biochemical reactions depending on the temperature. The catalytical functioning of the bacteria influences to a large extent the reaction speed. This means in other words that the reaction runs at high speed if the preferred conditions of a defined stem of bacteria are created. The preferred reaction conditions for a stem of bacteria comprise the temperature, the pH value and the feeding material. Special reactions can be favored to occur and accelerated by a defined feeding material offerred and by a defined temperature. Then the hydrolysis is nearly concluded as determined for example by the conductivity measurements and the determination of pH value, then the material is pumped off and led into a storage container. The conditions in the storage container favor the fermentation and therefore run very quickly. It is of course a simplification if one says that a process runs only in one container containing such a slush, however the running of a single process is the case to a large extent and is based on the preferred treatment of one stem of bacteria with respect to feeding and preferred temperature, which very much influence in the multiplication speed of the bacteria.

The methane gas yield depending on the starting materials is shown in table 1.

The biogas B is withdrawn from each fermenting machine in a controlled fashion, which biogas B is possibly available as a renewable energy carrier. The completely disintegrated biomass substrate is led from the last fermenting machine 9 into a hydro cyclone 10, wherein the separation of the residual liquid A is performed in the hydro cyclone 10. These residual components are usable in different production cycles and in fact, for example as a porosity providing agent as it concerns the solid part, or as process water as it concerns the liquid part.

Spacial separation of reaction containers

The spacial separation of the individual phases of the process in different vessels and reactors permits an easier control of the pH value and reduces the risk of an over acidification by the formation of free acids. A further important characteristic value is the concentration of lignin. Since lignin is not decomposed in the process, the relative lignin content increases in the solid material residue. The parts of solid material at the beginning of the process that is after the cutting and comminuting, amounts to eight percent by weight. When the parts of solids have decreased to 0.5 percent, the assumption is proper that the residue is exclusively lignin. Consequently the process of gas generation is terminated. According to conventional plants the state is achieved after 30 to 40 hours. In contrast, plants according to the present invention reach the termination stage after about 15 hours.

The anaerobic digestion apparatus

The apparatus of the invention essentially comprises a sequence of vessels for sequentially performing the chemical and biological disintegration of the biomass.

A series of vessels joined by appropriate piping, valves and pumps such as illustrated later down are used to realize the anaerobic digestion apparatus.. The vessels, preferably silo type tanks, have a preferred but are not limited to a height/diameter relationship encompassed between 1:1 and 5:1. The vessels might be double walled or feature other means of obtaining extended surface heat transfer between the biomass substrate and a heating medium such as steam or heating oil maintaining a low differential temperature, <50° C., between the heat transfer surface and the biomass substrate.

The first storage container is connected with a first pipe to the cutting plant 3. A third pipe connects the cutting plant 3 to a pump 3a. A second pipe connects the second storage container 2 to the third pipe and to the pump 3a. A fourth pipe connects the pump 3a to a pre-heater 4. A fifth pipe connects the heat exchanger 4a to the hydrolysis container 5, A sixth pipe connects the hydrolysis container 5 to a heat exchanger 6. A seventh pipe connects the heat exchanger 6 to the acidification container 7. An eighth pipe connects the acidification container 7 to a first biogas generator 8. A ninth pipe connects the first biogas generator 8 to the second biogas generator 9. A tenth pipe connects the second biogas generator to the hydro cyclone 10. An eleventh pipe for feedback connects the hydro cyclone 10 to the acidification container 7. A twelfth pipe for feedback connects the hydro cyclone 10 to the acidification container 5.

The source of the bacteria and enzymes

The generation of methane is followed by an aerobic after clearing of the residue. The enzymes remain essentially intact during this process. A further important feature of the method is the back feed of the liquid which still contains bacteria and enzymes. The bacteria multiply the during optimal conditions very quickly and the still present enzymes also help starting the reactions. The spacial separation and the special treatment of the bacteria involved shows clearly how positive this point affects the overall process.

The charging volume of the starting biomass is fed from the storage containers 1, 2 to the cutting plant 3 for the purpose of comminuting into smaller particle sizes and is then fed to a pre-heater 4 by way of a pump 3a, where the biomass is subjected to a heat addition (Ta—Tb) with the heat exchanger 4a. If required, water vapor V introduced by water vapor feed pipe 4b can be employed for this purpose, wherein the water vapor can be injected in the charging region or in the discharging region of the heat exchanger 4a, into the biomass or into the heat exchanger 4a itself.

The biomass is transported from the pre-heater 4 to the hydrolysis vessel 5. The biomass needs to be mixed continuously during hydrolysis either by a compulsory mixing system, mixing paddles for example, or by any other suitable mixing device. Gas of a gas mixer 5b can be used to mix the biomass during hydrolysis. In the case of mixing paddles the flow speed when measured at the outer wall of the hydrolysis vessel shall be in the range of $2r\pi=0,25$ to $1,25$.

In case an internal mixer such as tube mixer is employed with upwards or downwards flow direction, then however a downwards flow direction is to be preferred in order to avoid the formation of sedimentary deposits at the bottom of the hydrolysis vessel.

The hydrolyzed biomass is then transferred through a heat exchanger 6 and the seventh pipe into the acidification vessel 7 by means of a suitable pump such as a positive displacement or centrifugal pump, with a constant or intermittent flow. It has been found to be of advantage to interrupt mixing during acidification. It is preferred to transfer the hydrolyzed biomass from the bottom of the hydrolysis vessel 5 to the top of the acidification vessel 7. Acidification takes place at pH values in the range of 3 to 5 and at temperatures in the range of 25° C. to 65° C. Piping has to be dimensioned according to the capacity of the pump where flow speeds of 4 to 5 cm/sec are best suited for the purpose. Pumping with higher or lower flow speeds is nevertheless feasible and possible without any major detrimental effect on the process itself.

Following hydrolysis and acidification, the preparatory process of the biomass, the acidified biomass is fed to the methane generators 8, 9 either by overflow from the acidification vessel 7 or by a pump of the aforesaid type. In case of overflow this occurs whenever biomass is fed to the acidification vessel 7 from the hydrolysis vessel and hence the level in the acidification vessel 7 reaches the point of overflow. An overflow can either be achieved in a bottom/top, top/top or top/bottom layout. A feed by overflow into the methane generating vessels 8, 9 can only be achieved if the vessels are on the same level. In each other case a pump of the aforesaid type is to be used.

The hydrolysis vessel 5 as well as the following fermentation machines 7,8,9, are equipped with a vertically standing double walled tube 5a, wherein a cooling agent (Tb—Ta) or, respectively, a thermal medium circulates inside the double walled tube 5a for controlling the temperature. Such regulation might be achieved by increasing or decreasing the flow of the heat exchanger medium by means of automatically controlled valves or by increasing or decreasing the temperature of the heat exchanger medium itself. Use of electric heating systems similar in type to water heaters is not recommended due to the build up of deposits on the outside of the heating elements when in contact with the biomass. Such regulation is best achieved by tying the temperature gauges installed on each vessel into a possibly automatically controlled system. An electromechanical system would be possible as well as due to the relatively large volumes of biomass contained in the vessels regulation is slow due to inertia of the masses.

A complete plant can feature one or more hydrolysis vessels and/or one or more acidification vessels.

Should one or more hydrolysis vessels and one or more acidification vessels be used with the same pump, appropriate valving has to be provided. If more than one acidification vessel 7 is associated with a specific hydrolyzation vessel 5, then appropriate valving has to be installed. If a specified hydrolyzation vessel 5 is associated with a specific acidification vessel usually it is not necessary to provide valving as the pump will hinder backflow from the acidification vessel 7 into the hydrolysis vessel 5 at any time.

For both the hydrolysis and the acidification vessel, top, bottom or side mounted level gauges, temperature gauges and pH gauges are recommended in order to achieve optimal process data readings.

The vessels 8, 9 used for methane generation can either be clustered, for example two or more vessels will form a cluster that in turn will represent a single stage in the multi stage methane generation process, to form a single vessel. Clustered vessels will have the advantage of lower building costs as standard components can be used. Single or clustered vessels will form a cascade. The clusters or single vessels will be connected between them in a way similar to the one described above.

Of course, all phases of the invention method provide for the recording of the data concerning temperature, pressure, flow speed, and chemical composition for the purpose of specific process control, which recording of data allows a high degree of effectiveness concerning the generation of biogas, of sludges F and of residual liquids A, which can be employed without problems in different production processes.

The invention method and the corresponding apparatus plant enable the processing of biomasses of very different origin, consistency and chemical properties, wherein the problems of discharging of liquid residual materials and of thickened sludges are resolved by the complete disintegration of the organic material and wherein the biogas generated, as well as the obtained heat are made useful for the operation of the plant itself or, respectively, as a renewable energy for example for the operation of plants of different kinds.

It will be understood that each of the elements described above, or two or more together, may also find a useful application in other types of waste recovery system configurations and biomass processing procedures differing from the types described above.

While the invention has been illustrated and described as embodied in the context of a method and apparatus for anaerobic digestion of biomasses and for generation of biogas, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Summary Table of the Biogas Yield Depending on the Starting Materials

| Biomass | m³/k DS |
|---|---|
| Kitchen wastes | 0.7-1.3 |
| Biodegradeable packaging | 0.64 |
| Packaged food production wastes | 0.32-0.8 |
| Slaughterhouse wastes | 0.34-0.71 |
| Organic based oils and greases including lubricant oils | >0.5 |
| Fishing wastes | ~=0.5 |
| Differentiated waste collection | 0.40-0.58 |
| Potato wastes | ~=0.48 |
| Wastes from the production of drugs | 0.2-0.75 |
| Potato distillation residues | ~=0.46 |
| Beer production residues | 0.42-0.5 |
| Fruit distillation rasidues | 0.45 |
| Green waste | 0.35-0.46 |
| Sewage sludge | 0.39-0.41 |
| Manure | 0.22-0.55 |
| Paper and cardboard production wastes | 0.2-0.3 |

What is claimed as new and desired to be protected by Letters Patent is set forth in the appended claims:

1. A method for an anaerobic digestion of biomasses with a generation of biogas and sludge comprising
fragmenting a biomass;
separately hydrolyzing the fragmented biomass;
separately acidifying the hydrolyzed biomass;
separately generating methane from the acidified biomass, wherein the hydrolyzing, the acidifying, and the generating of methane are performed successively on the biomass; and wherein the hydrolyzing, the acidifying, and the generating of methane are performed in separate containers under specific measurement and control of temperature, of intermixing, of a pH value and of a pressure.

2. The method according to claim 1 further comprising
pre-heating the biomass with a heat exchanger (4a) and/or by way of injection of water vapor (V) prior to hydrolyzing,
wherein the hydrolyzing of the biomass is performed at a temperature between about 40 degrees centigrade and 100 degrees centigrade;
cooling the hydrolyzed biomass.

3. The method according to claim 2 further comprising
employing heat, which is led away during cooling (6), in one or in several phases (4,5,7,8,9) of the method or in another connected process for a pre-heating or heating.

4. The method according to claim 1 further comprising
feeding in of sludges (Fe) containing acid enzymes and produced at the end of the generating of methane under controlled conditions to the hydrolyzing of the biomass or to the acidifying of the biomass.

5. The method according to claim 1, further comprising
performing the acidifying by acid forming enzymes;
wherein the generating of methane is furnished under a subjection with specific methanogenus bacteria, wherein the specific methanogenus bacteria are present in a container for generating biogas, wherein specific conditions relating to temperature, pH value, intermixing and pressure prevail in the container for generating biogas and performing fermenting.

6. The method according to claim 1 further comprising
thickening sludges (F) occurring at a discharge outlet of a last methane generating machine (9) in a hydro cyclone (10) or by way of a centrifuge;
separating a residual liquid (A) from solid residues.

7. The method according to claim 1 further comprising
withdrawing biogas (B) produced during the acidifying and the generating of methane under controlled conditions from each of individual fermentation machines.

8. A method for an anaerobic digestion of biomasses with a generation of biogas and sludge comprising
fragmenting a biomass;
separately hydrolyzing the fragmented biomass in a first reaction container;
measuring and controlling temperature, intermixing, pH-value and pressure in the first reaction container;
successively and separately acidifying the hydrolyzed biomass in a second reaction container;
measuring and controlling temperature, intermixing, pH-value and pressure in the second reaction container;
successively separately generating methane from the acidified biomass in a third reaction container,
measuring and controlling temperature, intermixing, pH-value and pressure in the third reaction container.

9. The method according to claim 8 further comprising
pre-heating the biomass with a heat exchanger (4a) and/or by way of injection of water vapor (V) prior to hydrolyzing,
wherein the hydrolyzing of the biomass is performed at a temperature between about 40 degrees centigrade and 100 degrees centigrade;
cooling the hydrolyzed biomass.

10. The method according to claim 9 further comprising
employing heat, which is led away during cooling (6), in one or in several phases (4,5,7,8,9) of the method or in another connected process for a pre-heating or heating.

11. The method according to claim 8 further comprising
feeding in of sludges (Fe) containing acid enzymes and produced at the end of the generating of methane under controlled conditions to the first container hydrolyzing the biomass or to the second container acidifying the biomass.

12. The method according to claim 8, further comprising
performing the acidifying by acid forming enzymes;
wherein the generating of methane is furnished under a subjection with specific methanogenus bacteria, wherein the specific methanogenus bacteria are present in the third container for generating biogas, wherein specific conditions relating to temperature, pH value, intermixing and pressure prevail in the third container for generating biogas and performing fermenting.

13. The method according to claim 8 further comprising
thickening sludges (F) occurring at a discharge outlet of a last methane generating machine (9) in a hydro cyclone (10) or by way of a centrifuge;
separating a residual liquid (A) from solid residues.

14. The method according to claim 8 further comprising
withdrawing biogas (B) produced during the acidifying and the generating of methane under controlled conditions from each of individual fermentation machines.

15. An anaerobic decomposition apparatus comprising
a hydrolyzator (5) is furnished for an anaerobic digestion of a biomass substrate;
an acidifying vessel (7) connected to the hydrolyzator (5) in series;
a vessel for generating biogas (8) connected to the acidifying vessel and wherein, the hydrolyzator (5) as well as also the vessels are equipped with a heat exchanger (4a), with mechanical, hydraulic, or gas mixers (5b) and with sensors (Tf) or detectors for the determination of values relating to temperature, with sensors (Ph) or detectors for the determination of values relating to the pH value, with sensors (P) or detectors for the determination of values relating to the pressure, with sensors (M) or detectors for the determination of values relating to the degree of mixing, and wherein the heat exchanger (4a), the gas mixer (5b), the withdrawal of biogas and an introduction of fed back sludges (Fe) are operated depending on the recited determined values and of specific requirements of a flora of bacteria operating in the hydrolysator (5) and in the vessels (7,8,9).

16. The apparatus according to claim 15 further comprising a preheater (4) disposed in front of the hydrolyzator (5) and furnished with a heat exchanger (4a) and a device for the injection (4b) of water vapor in a position ahead of the heat exchanger (4a), after the heat exchanger (4a), or in an intermediate position.

17. The apparatus according to claim 15 further comprising a heat exchanger (6) furnished behind the hydrolyzator (5) for cooling of the hydrolyzed biomass substrate.

18. The apparatus according to claim 15 further comprising
an eleventh pipe connecting an output of the vessel for generating methane to the hydrolyzator for performing a controlled feedback (Fe) of sludges, which sludges are separated at the end of the apparatus; or
a twelfth pipe connecting an output of the vessel for generating methane to the acidifying vessel (7) for performing a controlled feedback (Fe) of sludges, which sludges are separated at the end of the apparatus.

19. An anaerobic decomposition apparatus comprising
a hydrolysis vessel (5) for an anaerobic digestion of a biomass substrate;
a first heat exchanger attached to the hydrolysis vessel;
a first mixer attached to the hydrolysis vessel;
a first detector (Tf) for detecting temperature in the hydrolysis vessel;
a first detector (Ph) for detecting a pH-value in the hydrolysis vessel;
a first detector (P) for detecting pressure in the hydrolysis vessel;
an acidifying vessel (7) connected to the hydrolysis vessel (5) in series;
a second heat exchanger attached to the acidifying vessel;
a second mixer attached to the acidifying vessel;
a second detector (Tf) for detecting temperature in the acidifying vessel;
a second detector (Ph) for detecting a pH-value in the acidifying vessel;
a second detector (P) for detecting pressure in the acidifying vessel;
a vessel for generating biogas (8) connected to the acidifying vessel;
a third heat exchanger attached to the vessel for generating biogas (8);
a third mixer attached to the vessel for generating biogas (8);
a third detector (Tf) for detecting temperature in the vessel for generating biogas (8);
a third detector (Ph) for detecting a pH-value in the vessel for generating biogas (8);
a third detector (P) for detecting pressure in the vessel for generating biogas (8).

20. The apparatus according to claim 19 further comprising
a first detector (M) for detecting a degree of mixing in the hydrolysis vessel;
a second detector (M) for detecting a degree of mixing in the acidifying vessel;
a third detector (M) for detecting a degree of mixing in the vessel for generating biogas;
a withdrawal port for withdrawing biogas and attached to the vessel for generating biogas;
a sixth pipe connecting the hydrolysis vessel (5) to the second heat exchanger (6); a seventh pipe connecting the second heat exchanger (6) to the acidifying vessel (7);
an eighth pipe connecting the acidifying vessel (7) to the vessel (8) for generating biogas;
a first feedback conduit connecting the vessel for generating biogas to the hydrolysis vessel;
a second feedback conduit connecting the vessel for generating biogas to the acidifying vessel; vessel;
and
wherein the first heat exchanger (4a), the mixer (5b), the withdrawal of biogas and an introduction of fed back-sludges (Fe) are operated depending on the detected values and of the specific requirements of the flora of bacteria operating in the hydrolysis vessel (5), in the acidifying vessel (7), and in the vessel (8,9) for generating biogas.

* * * * *